(12) United States Patent
Ishihara et al.

(10) Patent No.: US 7,014,650 B2
(45) Date of Patent: Mar. 21, 2006

(54) PIN FOR FORMING A HOLE FOR INSERTING AN INDWELLING NEEDLE

(75) Inventors: Jun Ishihara, Fuji (JP); Shigeki Toma, Okinawa-ken (JP); Yoshihiko Sano, Osaka (JP); Toshiaki Masuda, Osaka (JP); Masashi Ishida, Kyoto (JP); Kazuyoshi Harada, Osaka (JP)

(73) Assignee: Nipro Corporation, Osaka (JP)

( * ) Notice: Subject to any disclaimer, the term of this patent is extended or adjusted under 35 U.S.C. 154(b) by 123 days.

(21) Appl. No.: 10/119,692

(22) Filed: Apr. 11, 2002

(65) Prior Publication Data
US 2002/0151905 A1    Oct. 17, 2002

(30) Foreign Application Priority Data
Apr. 13, 2001   (JP) .............................. 2001-115747

(51) Int. Cl.
*A61B 17/04* (2006.01)
*A61B 17/00* (2006.01)
(52) U.S. Cl. .............................. 606/213; 606/1; 606/80
(58) Field of Classification Search ................ 604/175, 604/256, 28, 533; 606/1, 213, 192, 167, 606/164, 80; 600/32; 128/864, 8
See application file for complete search history.

(56) References Cited

U.S. PATENT DOCUMENTS

| | | | | |
|---|---|---|---|---|
| 5,192,301 A | * | 3/1993 | Kamiya et al. | 606/213 |
| 5,326,350 A | | 7/1994 | Li | 623/11 |
| 5,372,583 A | | 12/1994 | Roberts et al. | 604/51 |
| 5,403,336 A | * | 4/1995 | Kieturakis et al. | 606/167 |
| 5,904,703 A | | 5/1999 | Gilson | 606/213 |
| 6,228,088 B1 | * | 5/2001 | Miller et al. | 606/80 |
| 6,270,515 B1 | * | 8/2001 | Linden et al. | 606/213 |

FOREIGN PATENT DOCUMENTS

| | | |
|---|---|---|
| DE | 44 29 230 A1 | 2/1996 |
| DE | 196 39 615 A1 | 4/1998 |
| NL | 6 614 673 A | 4/1968 |
| WO | 97/06734 A1 | 2/1997 |
| WO | 99/52444 A1 | 10/1999 |

* cited by examiner

*Primary Examiner*—Nicholas D. Lucchesi
*Assistant Examiner*—Roz Maiorino
(74) *Attorney, Agent, or Firm*—Kubovcik & Kubovcik

(57) ABSTRACT

A pin for forming a hole for inserting an indwelling needle 1 which includes a columnar inserting member 11 and an insertion stopping member 12 provided on a proximal end of the inserting member 1, the insertion stopping member 12 being provided with a recess 121 as a holding part.

5 Claims, 1 Drawing Sheet

PIN FOR FORMING A HOLE FOR INSERTING AN INDWELLING NEEDLE

TECHNICAL FIELD OF THE INVENTION

This invention relates to a pin for forming a hole extending from the surface of the skin of a human body to a wall of a blood vessel or to a position very close to the blood vessel.

BACKGROUND OF THE INVENTION

A hemodialysis patient needs to be subjected to hemodialysis at a rate of 2 to 3 times a week. Every time the patient is subjected to dialysis, piercing into a blood vessel of the patient with a indwelling needle causes the patient to suffer considerable pain.

The applicant of the present invention has already proposed a device for forming a hole for inserting an indwelling needle (refer to Japanese Patent Laid-Open No. 176009/2000) for decreasing such puncture pain to a minimum level. The device has a distal end and a proximal end, and includes a hollow body having an inner cavity through which a guide wire can be inserted. At least the distal end portion of the device, which is inserted into a human body, is formed of a tubular body difficult to bend to or to be easily collapsed. A member for closing an opening portion of the cavity is detachably provided on the proximal end portion. After the device is indwelt for several days in a location extending from the surface of the skin to a blood vessel, a hole serving as a passage for inserting an indwelling needle is formed. In order to conduct hemodialysis, an indwelling needle is inserted into the hole, so that the puncture pain which the patient subjected to hemodialysis suffers is substantially alleviated.

However, in order to indwell the device for forming a hole for inserting an indwelling needle in a human body, the following complicated operations have been needed.

(1) After a general indwelling needle for dialysis comprising an inner needle and an outer needle is pierced into a shunt portion in a blood vessel of a patient, the inner needle is pulled out and the outer needle is indwelt in an inside of the blood vessel.

(2) A guide wire is then inserted into the outer needle and, thereafter, the outer needle is pulled out and the guide wire alone is indwelt inside of the blood vessel.

(3) A device for forming a hole for inserting an indwelling needle is introduced into the inside of the blood vessel along the guide wire and indwelt therein.

Such complicated operations for indwelling the device have been a considerable burden on medical personnel. Moreover, while the device for forming a hole for inserting an indwelling needle indwells in the human body, there is a risk that the device will hurt the wall of the blood vessel. Therefore, it is necessary for the patient to lie still. These problems make it difficult to indwell the device for forming a hole for inserting an indwelling needle into a patient for a long period of time.

The present invention has been made in view of the above-mentioned circumstances, and provides a device for forming a hole for inserting an indwelling needle capable of forming a hole very easily.

SUMMARY OF THE INVENTION

The inventors have carried out a procedure employing a pin, which has a columnar inserting member rounded at a distal end thereof and a length substantially equal to or somewhat smaller than a distance between the surface of the skin and a wall of a blood vessel, and forming a part, which extends from the surface of the skin to the wall of the blood vessel or to a position very close the wall of the blood vessel, in a hole, or opening, for inserting an indwelling needle extending from the surface of the skin to an inside of the blood vessel. As a result, it has been found that a hole, or opening, for inserting an indwelling needle extending from the surface of the skin to the inside of the blood vessel can be formed by piercing the wall of the blood vessel only once with a piecing needle having a sharp distal end, without restricting the daily activities of the patient, and the present invention was completed.

Namely, the present invention is directed to a pin for forming a hole between the skin and a blood vessel for inserting an indwelling needle, the pin including a columnar inserting member having a distal rounded end and an insertion stopping member provided on a proximal end of the inserting member, the insertion stopping member being provided with a holding part.

DESCRIPTION OF THE DRAWINGS

Referring to the preferred embodiments and attached drawings, a pin of the present invention will hereinafter be described. However, the present invention is not limited thereto.

DETAILED DESCRIPTION OF THE INVENTION

Figure 1:
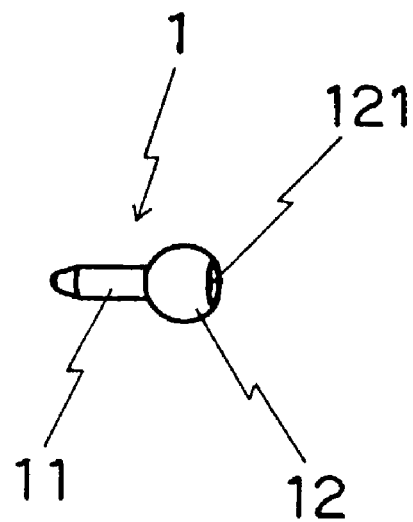
FIG. 1 is a perspective view showing an example of a pin for forming a hole for inserting an indwelling needle according to the present invention.

In a pin according to this invention, a term "distal end" means an end at which a patient is pierced and a term "proximal end" means the end opposite to the distal end.

The pin 1 of the present invention comprises a columnar inserting member 11, an insertion stopping member 12 provided on a proximal end of the inserting member 11, wherein the insertion stopping member 12 is provided with a recess 121 as a holding part.

The columnar inserting member 11 is rounded at the distal end thereof. When a hole is formed by putting this inserting member 11 into a part of a tissue which is pierced with a indwelling needle for dialysis, neither deviation of the path along which the hole is formed nor the hurting of other parts of the tissue occurs owing to the above-mentioned shape of the inserting member. In order to form a hole substantially large enough to enable an indwelling needle having a non-sharp distal end to be inserted thereinto, the outer diameter of the inserting member 11 is preferably 0.5 to 3.0 mm, and more particularly 1.0 to 2.0 mm. During indwelling of the pin 1 in the hole, the distal end of the inserting member 11 reaches only a blood vessel wall or a position very close to the blood vessel. Therefore, the length of the inserting member 11 is preferably set to 3 to 20 mm or, more preferably, to 4 to 6 mm so that the inserting member 11 does not press against the blood vessel wall.

The material of which inserting member 11 is formed includes a synthetic resin, such as polypropylene, polycarbonate, ABS resin, polyethylene, polytetrafluoroethylene, polysulfone, etc., and a metal, such as stainless steel, etc. In addition, these materials coated with an antithrombotic material can also be preferably employed.

The insertion stopping member 12 is provided so as to prevent the pin 1 from being buried in the skin and to fix the pin easily during indwelling of the pin. The shapes of the insertion stopping member 12 may include a spherical shape, a flat plate-like shape, a conical shape, an egg-like shape, etc. The spherical shape is preferably employed. In the case that the insertion stopping member 12 has a spherical shape, a diameter of the insertion stopping member 12 is preferably about 2 mm to about 10 mm and, more preferably, 3 to 5 mm. The diameter of the insertion stopping member 12 is greater than the diameter of the inserting member 11 and, preferably, is at least 0.2 mm greater than the diameter of the inserting member 11. Although the inserting member 11 and the insertion stopping member 12 are generally molded integrally by injection molding, they may also be molded separately and then integrated together. The material used to form the insertion stopping member 12 may be identical with that of the inserting member 11, or it can be a soft material, such as polyvinyl chloride, a rubber-like elastic body, etc.

When the inserting member 11 is inserted into a human, the insertion stopping member 12 can be fixed on a surface of the skin by using adhesive or by covering with a sheet having adhesion, for example, an adhesive tape.

Figure 2:
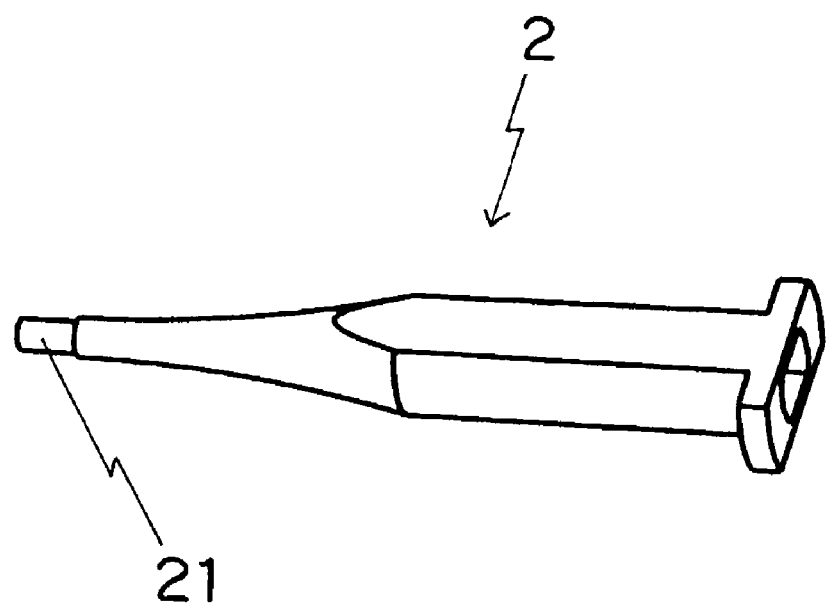
FIG. 2 is a perspective view showing an example of an auxiliary operating member used in conjunction with a pin of the present invention.

The pin 1 according to the present invention is very small, and it is difficult for medical personnel wearing gloves to hold the pin with the finger tips. Therefore, it is preferable that an auxiliary operating member 2 having a total length of about 3 cm to about 10 cm as shown in FIG. 2 is used. To meet the requirement, the insertion stopping member 12 is provided with a holding part for enabling the pin to be held by means of the auxiliary operating member 2. For example, a recess 121 provided in the proximal end of the insertion stopping member 12 as shown in FIG. 1 can be employed as the holding part. In order to indwell the pin 1, a distal end portion 21 of a small diameter of the auxiliary operating member 2 is inserted into the recess 121 of the pin 1. The holding part is not limited to the recess 121 shown in FIG. 1, and, for example, a pair of recesses may be provided in a side wall of the insertion stopping member 12. In this case, something like a pair of tweezers is preferably employed as the auxiliary operating member 2.

An inner diameter of the recess 121 of the pin 1 and an outer diameter of the distal end portion 21 of the auxiliary operating member 2 are set substantially equal, and the recess 121 is fitted with the distal end portion 21. A means of engaging the recess 121 and the distal end portion 21 may also be a means for engaging a projection provided on the recess 121 and a depression provided on the distal end portion 21, a means for engaging a depression provided on the recess 121 and a projection provided on the distal end portion 21, or a means for engaging screw threads provided on the recess 121 and the distal end portion 21, respectively.

A method of using the pin 1 according to the present invention is hereinafter described.

First, an indwelling needle for dialysis comprising an inner needle having a sharp distal end and an outer plastic needle is pierced into a vein of a patient, and hemodialysis is conducted. After hemodialysis is completed, the indwelling needle is pulled out, and a passage is formed as a wound.

The pin 1 is preferably inserted into the passage using the auxiliary operating member 2. A dilator for dilating the passage may be used during the insertion of the pin 1. When the insertion stopping member 12 of the pin 1 touches a surface of the skin of the patient and insertion of the pin 1 is stopped, the insertion stopping member 12 is gripped by the patient's hand and the auxiliary operating member 2 is removed. The insertion stopping member 12 is covered with an adhesive tape and the pin 1 is indwelt for several days. After the pin 1 is pulled out, a part (passage), which extends from the surface of the skin of the patient to a blood vessel wall or to a position very close to the blood vessel wall is formed, in a hole for inserting a indwelling needle to be provided so as to extend from the surface of the skin to the inside of the blood vessel.

When a piercing needle having a sharp distal end is pierced into the blood vessel wall just once, a hole for inserting an indwelling needle which extends from the surface of the skin to the inside of the blood vessel is completed. In general, the hole not in use is closed with coagulated or semi-coagulated blood, and a surface of a skin near the hole is scabbed small. In order to indwell the indwelling needle for dialysis in the hole, the scab is removed with the tip of the indwelling needle for dialysis or the like, and this indwelling needle can be inserted into the hole.

It is preferable to employ an indwelling needle for dialysis which is not sharp at the distal end thereof as the indwelling needle for dialysis to be inserted into this hole. The use of such an indwelling needle does not give pain to the patient.

EFFECTS OF THE INVENTION

Owing to the pin according to the present invention, the present invention is capable of forming a part, which extends from a surface of a skin of a patient to a blood vessel wall or to a position very close to the blood vessel, in a hole for inserting an indwelling needle to be provided so as to extend from the surface of the skin to the inside of a blood vessel, safely and without restricting daily activities of the patient. When the hole is formed, an indwelling needle for dialysis not sharp at a distal end thereof can be employed, so that the skin and the blood vessel of the patient are not hurt even during the insertion of the indwelling needle for dialysis into the hole, and the patient's pain can be lightened.

What is claimed is:

1. A pin comprises a columnar inserting member for forming a hole between a surface of a skin and a blood vessel for inserting an indwelling needle and which is solid and has an outer diameter of 0.5 to 3.0 mm and a length of 3 to 20 mm and has a rounded distal end, pin insertion stopping member provided on a proximal end of the inserting member, said pin insertion stopping member being spherically shaped and having a diameter of 2 to 10 mm and which greater than diameter of the inserting member, and holding means provided insertion stopping member for cooperating with means for holding said pin.

2. A pin according to claim 1 wherein the outer diameter of the columnar inserting member is 1.0 to 2.0 mm, and the length thereof is 4 to 6 mm.

3. A pin according to claim 1, wherein the insertion stopping member is spherically shaped and has a diameter of 3 to 5 mm and which is greater than a diameter of the inserting member.

4. A pin comprises a columnar inserting member for forming a hole between a surface of a skin and a blood vessel for inserting an indwelling needle and which solid and has an outer diameter of 0.5 to 3.0 mm and length of 3 to 20 mm and has distal end that rounded when viewed cross section of the distal end along the axis of the pin, a pin insertion stopping member provided proximal end inserting member, said pin insertion stopping member being spherically shaped and having greater than diameter of the inserting member, and holding means provided on the insertion stopping member for cooperating with means for holding said pin.

5. A pin comprises columnar inserting member for forming a hole between a surface of a skin and a blood vessel for inserting an indwelling needle and which is solid and not threaded and has an outer diameter of 0.5 to 3.0 mm and a length of 3 to 20 mm and a rounded distal end, a pin insertion stopping member provided on a proximal end of the inserting member, said pin insertion stopping member being spherically shaped and having a diameter 2 to 10 mm and which is greater than diameter of the inserting member, and a holding means provided on the insertion stopping member for cooperating with means for holding said pin.

* * * * *